United States Patent
Keesling

(10) Patent No.: US 9,743,860 B2
(45) Date of Patent: Aug. 29, 2017

(54) USE OF LIGHT TRANSMISSION THROUGH TISSUE TO SENSE JOINT FLEXURE

(71) Applicant: APPLIED MINDS, LLC, Glendale, CA (US)

(72) Inventor: Michael Keesling, Agoura Hills, CA (US)

(73) Assignee: Applied Invention, LLC, Glendale, CA (US)

( * ) Notice: Subject to any disclaimer, the term of this patent is extended or adjusted under 35 U.S.C. 154(b) by 543 days.

(21) Appl. No.: 14/076,160

(22) Filed: Nov. 8, 2013

(65) Prior Publication Data

US 2015/0130696 A1 May 14, 2015

(51) Int. Cl.
*A61B 5/107* (2006.01)
*G06F 3/01* (2006.01)
*A61B 5/00* (2006.01)

(52) U.S. Cl.
CPC .......... *A61B 5/1071* (2013.01); *A61B 5/4528* (2013.01); *G06F 3/014* (2013.01); *A61B 5/6806* (2013.01)

(58) Field of Classification Search
CPC ... A61B 5/1071; A61B 5/4528; A61B 5/6825; A61B 5/6826; A61B 2562/0238; A61B 2562/0242; G06F 3/014
See application file for complete search history.

(56) References Cited

U.S. PATENT DOCUMENTS

| | | | | |
|---|---|---|---|---|
| 4,542,291 A * | 9/1985 | Zimmerman | ........ | A61B 5/1126 250/231.1 |
| 5,184,009 A * | 2/1993 | Wright | .................. | G02B 6/264 250/221 |
| 6,110,130 A * | 8/2000 | Kramer | ................ | A61B 5/1071 600/587 |
| 6,380,923 B1 * | 4/2002 | Fukumoto | ............... | G06F 1/163 341/22 |
| 8,909,500 B2 * | 12/2014 | Heijkants | ............. | A61B 5/1071 702/151 |
| 9,104,271 B1 * | 8/2015 | Adams | .................. | G06F 3/0426 |
| 2004/0046737 A1 * | 3/2004 | Numazaki | ............. | G06F 3/0304 345/156 |
| 2004/0263473 A1 * | 12/2004 | Cho | ........................ | G06F 3/014 345/156 |
| 2009/0059206 A1 * | 3/2009 | Churchill | ............. | G01B 11/002 356/72 |
| 2010/0286950 A1 * | 11/2010 | Heijkants | ............. | A61B 5/1071 702/151 |

(Continued)

*Primary Examiner* — Adam J Eiseman
(74) *Attorney, Agent, or Firm* — Michael A. Glenn; Perkins Coie LLP

(57) ABSTRACT

Various embodiments relate to apparatuses and methods of using light transmission thought living tissue, such as a finger, to detect the flexure of a joint. Light is introduced into the tissue at one point, passes through the tissue, and exits the tissue at a second point where a sensor receives the light as it exits the tissue. Transmission of light through living tissue such as a finger can be affected by movement of the finger. As the finger flexes and, for example, the joints of the finger change angle, the characteristics of the light exiting the tissue, such as the intensity of the light, can change. These changes in characteristics can be used as an indirect means of determining the flexure of the joint.

9 Claims, 7 Drawing Sheets

(56) References Cited

U.S. PATENT DOCUMENTS

| | | | |
|---|---|---|---|
| 2011/0129124 A1* | 6/2011 | Givon | G06F 3/011 382/107 |
| 2013/0197399 A1* | 8/2013 | Montgomery | A61B 5/1121 600/595 |
| 2014/0098018 A1* | 4/2014 | Kim | G06F 3/014 345/156 |
| 2015/0309563 A1* | 10/2015 | Connor | G06F 3/011 73/865.4 |

* cited by examiner

USE OF LIGHT TRANSMISSION THROUGH TISSUE TO SENSE JOINT FLEXURE

STATEMENT OF GOVERNMENT RIGHTS

This invention was made with Government support under Contract No. GS00Q09BGD0013/GST0810BP0059 awarded by the U.S. Air Force. The United States Government may have certain rights in the invention.

CROSS-REFERENCE TO RELATED APPLICATIONS

The United States Non-Provisional application filed herewith on the same date and entitled "Use of Light Transmission Through Compressed Tissue to Detect Force" is hereby incorporated by reference for all purposes in its entirety.

FIELD OF TECHNOLOGY

The present disclosure relates to detecting the flexure of joints and the use of light transmission and reception through living tissue.

BACKGROUND

Data gloves are computer interface devices which characterize the pose and configuration of a human hand. This enables gesture recognition, motion capture, robotic control, data entry, and other functions. For example, a user can operate a computer or other device by making gestures without physical contact. Data gloves and other applications need to measure joint angles.

Existing solutions for measuring joint angles often rely on thin films and compressible fibers/sensors, which are delicate. When used in a data glove application, the thin films and sensors are subject to mechanical wear due to the user's hand movements. Being delicate, the thin films and sensors are susceptible to failure due to this mechanical wear. It is desirable to determine the angle of a joint with devices that are sufficiently robust to withstand the mechanical wear brought on by usage in data glove applications.

Some applications require the measure of joint angles in harsh environments. For example, an application may measure joint angles with the joint immersed in water. It is desirable that devices for determining joint angle be sufficiently robust to work reliably in harsh environments.

SUMMARY

Transmission of light through living tissue, such as a finger, can be affected by movement of the finger. Flexure of a finger, such as can happen when alternating between opening a hand and then making a fist, changes the position of the finger and deforms the tissue. Movement of a joint of a finger also changes the angle of the top of the finger on either side of the joint. For example, when a finger is straight, the top of the finger runs parallel on both sides of the joint. As a person bends his or her finger, an angle develops between the top of the finger on either side of the joint. If a person fully bends his or her finger, an angle of approximately 90 degrees is formed between the top of the finger on either side of the joint. One method of determining flexure of a joint is to determine the angle of a joint. As one having ordinary skill in the art will appreciate, determining flexure of a joint can be done using methods other than determining the angle of the joint.

A light emitter can be placed on top of the finger on one side of the joint and can send light into the finger at a 45 degree angle towards the joint. A light sensor can be placed on the top of the finger on the other side of the joint, the light sensor configured so that it receives light coming from a 45 degree angle towards the joint. When the finger is straightened and held parallel to the ground, the emitter emits light at a 45 degree angle and sends the light into the finger, and much of the light exits the bottom of the finger approximately under the joint. Resultantly, the sensor does not detect much light. When the finger is bent to approximately 90 degrees, the emitter emits and sends light that is now approximately parallel to the light that is received by the sensor. Resultantly, there is a significant increase in the amount of light detected by the sensor. This change in the intensity of the light as detected by the sensor can be used as an indirect way to determine the joint flexure of the finger.

Further, as the finger flexes and the joints of the finger change angle, the characteristics of tissue between two points on the skin can change, which can change the transmission of light between these two points. For example, the compression of the tissue can change, and, since the compression of tissue affects the transmission of light through the tissue, the light transmission between the two points can be affected. As another example, the tissue can deform, changing the distance and amount of tissue between the two points, which also affects transmission of light between the two points. These changes in characteristics and the associated changes in light transmission can be used as an indirect means of determining the angle of the joint.

The disclosed technology can provide an alternative to electromechanical methods that use wires which are susceptible to wear induced failure with repeated flexing. A flexible medium, such as optical fiber, can be used to send the light. Replacing the wires of the electromechanical method with such a medium can enable higher reliability and improved robustness. For example, this replacement of the wires can enable locating all electronics in a sealed container where the electronics can be protected from the environment. Additionally, a flexible medium for sending light can be less susceptible to failures due to repeated flexing as compared to wires, and does not have to be electromagnetically shielded.

Furthermore, since the light can be sent over the clear medium, the sealed container containing the electronics can be located away from the joint. For example, the electronics container can be placed on the back of the hand or even further up the arm away from the finger joint. This can enable improved performance in harsh environments, as the electronics can be kept away and protected from the harsh environment.

The disclosed technology enables the determination of flexure of a joint in living tissue. Some embodiments include a light source, a light sensing device, a processing device, and a supporting object. Light from the light source is introduced into the living tissue. The light sensing device is configured to sense the light exiting the living tissue. The processing device is configured to determine the flexure of the joint based at least in part on one or more characteristics of the light exiting the living tissue. The supporting object is to provide mechanical support for at least a portion of the apparatus. Some embodiments further include a first optical fiber and a second optical fiber. The first optical fiber is configured to send the light from the light source to a point of introduction of the light into the living tissue. The second optical fiber configured to send the light from a point of exit of the light from the living tissue to the light sensing device.

In some embodiments, the supporting object is a glove configured to be worn by a human hand and the living tissue comprises the human hand. The portion of the apparatus for which the glove provides the mechanical support is at least the first optical fiber and the second optical fiber. In some embodiments, the light source is configured to be located at a point of introduction of the light into the living tissue. In some embodiments, the light sensing device is configured to be located at a point of exit of the light from the living tissue. In some embodiments, the supporting object is a glove configured to be worn by a human hand and the living tissue comprises the human hand. The portion of the apparatus for which the glove is configured to provide the mechanical support is at least the light source and the light sensing device.

In some embodiments, the supporting object is a body suit configured to be worn by a human and the living tissue comprises the body of the human. In some embodiments, the one or more characteristics include an intensity of the light exiting the living tissue. In some embodiments, the light source generates infrared-spectrum light and the light sensing device senses infrared-spectrum light. In some embodiments, the light source is a light-emitting diode. In some embodiments, the light source is an infrared-spectrum light-emitting diode. In some embodiment, the configuration of the processing device to determine the flexure further includes configuration to determine an angle of the joint.

Flexure of a joint in living tissue can be determined using a method. Light can be introduced into the living tissue and can be received exiting the living tissue. Flexure of the joint can be determined based at least in part on one or more characteristics of the received light. In some embodiments, the light introduced into the living tissue is generated by a light source, and the light exiting the living tissue is received by a light sensing device. In some embodiments, the light introduced into the living tissue is sent from the light source to a point of introduction of the light into the living tissue by a first optical fiber. The light received by the light sensing device is sent from a point of exit of the light from the living tissue to the light sensing device by a second optical fiber.

The method for determining the flexure of the joint can further comprise calibration of an apparatus based at least in part on the one or more characteristics of the light exiting the living tissue. In some embodiments, the one or more characteristics includes an intensity of the light. In some embodiments, the calibration, when the joint is part of an appendage, can further comprise sensing a first light level while the appendage is in a straightened position, sensing a second light level while the appendage is in a bent position, and computing a correlation between the flexure of the joint and the received light, the computed light level based at least in part on the sensed first light level and the sensed second light level.

In some embodiments, the calibration can further comprise sensing an ambient light level while the light generation device is not generating any light, and the computing the correlation can further be based at least in part on the sensed ambient light. In some embodiments, the calibration can further comprise sensing an intermediate light level while the appendage is in a position between the straightened position and the bent position, and the computing the correlation can further be based at least in part on the sensed intermediate light level. In some embodiments, the determining the flexure of the joint can further comprise computing the angle of the joint based at least in part on the computed correlation. In some embodiments, the appendage is an arm of a human and the appendage is straightened when the arm is extended above the head of the human. The arm is bent when the arm is lowered from the straightened position. In some embodiments, the determining the flexure of the joint further includes determining an angle of the joint.

BRIEF DESCRIPTION OF THE DRAWINGS

Embodiments of the present invention will be described and explained through the use of the accompanying drawings in which.

DETAILED DESCRIPTION

Figure 1:
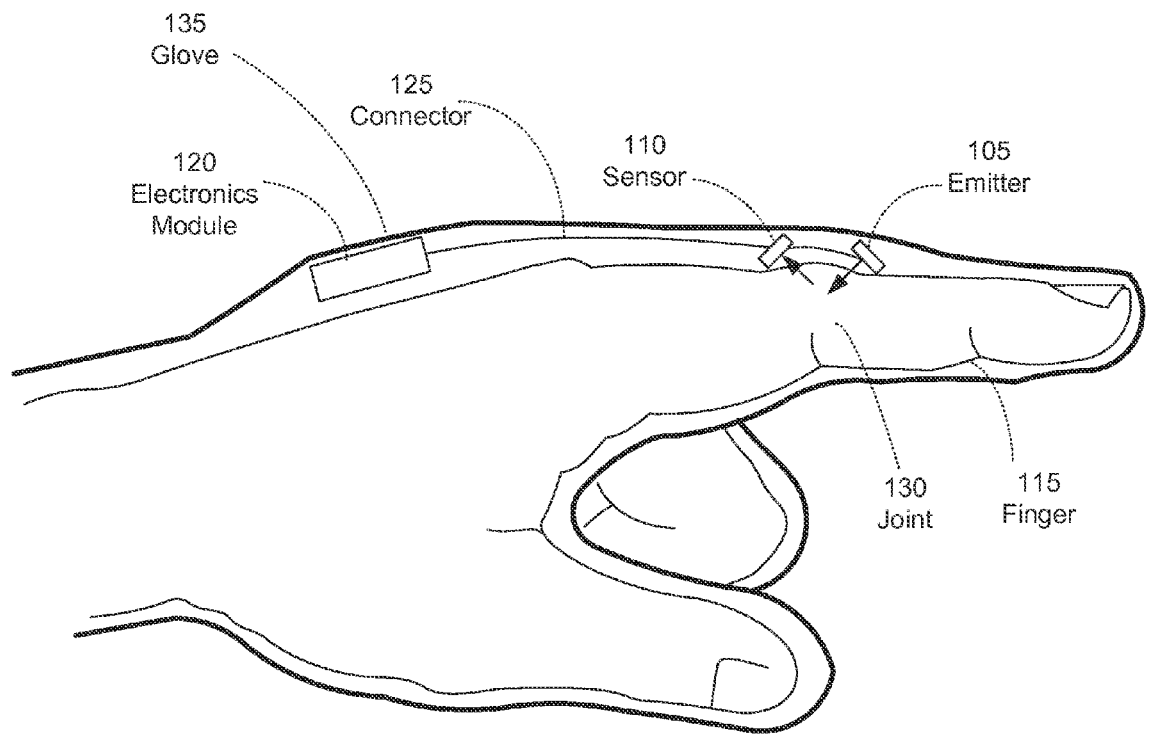
FIG. 1 illustrates an apparatus for determining an angle of a joint in a finger, shown with the finger straightened.

FIG. 1 illustrates an apparatus for determining an angle of a joint in a finger, shown with the finger straightened. As illustrated in FIG. 1, the apparatus includes emitter 105, sensor 110, electronics module 120, connector 125, and glove 135. Electronics module 120 is coupled to emitter 105 and sensor 110 by connector 125. Electronics module 120 provides power to and can communicate with emitter 105 and sensor 110 via connector 125.

Glove 135 can provide a mechanical support and attachment for any of electronics module 120, emitter 105, sensor 110, and connector 125, such that these components will remain with glove 135 when removed from a hand, and that putting on glove 135 can cause these components to be located at appropriate locations on the hand. Connector 125 can be two sets of wires, one set of wires coupling electronics module 120 to emitter 105, and a second set of wires coupling electronics module 120 to sensor 110. Emitter 105 can be an infrared-spectrum light-emitting diode (LED) and sensor 110 can be a sensor that senses the infrared light emitted by an infrared-spectrum LED.

There are at least two methods of sending light through tissue, the transmission method and the reflectance method. Sending light can include transmitting light, guiding light, conveying light, emitting light, reflecting light, and/or carrying light. In the transmission method, the emitter and sensor are placed on different locations on the skin with the tissue in between. The emitter can send light into the tissue at one point on the skin, the light passes through the tissue, and the sensor can receive the light exiting the tissue at a second different point on the skin. In the reflectance method, light emitted by the emitter and sent into the tissue is reflected and scattered, and the sensor senses primarily this reflected and scattered light rather than light passing directly through the tissue. For example, light from an emitter can enter the tissue. The tissue and the skin on the other side of the tissue can reflect and/or scatter the light. The sensor can be placed such that it receives primarily the scattered and reflected light. One example of a placement where the sensor would utilize the reflectance method would be if the emitter and sensor were both placed at adjacent locations on the skin of a finger.

Figure 2:
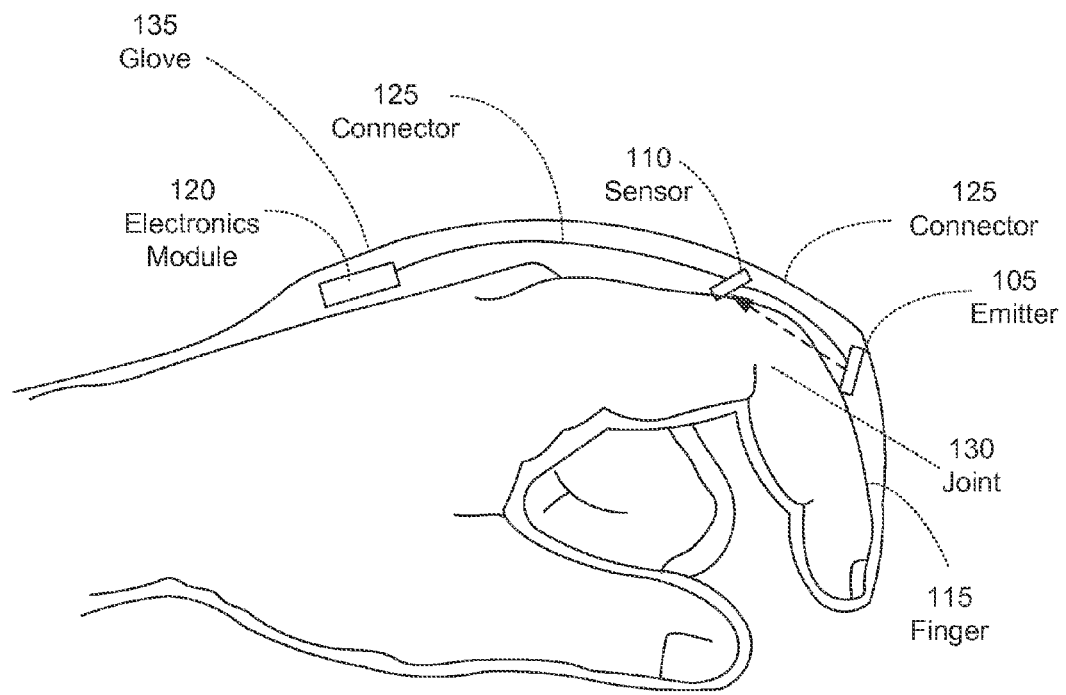
FIG. 2 illustrates an apparatus for determining an angle of a joint in a finger, shown with the finger bent.

The apparatus of FIG. 1 can use both the transmission and reflectance methods. For example, the movement of joint 130 changes the angle of the top of finger 115 on either side of joint 130. When finger 115 is straightened, as is illustrated in FIG. 1, the top of finger 115 runs parallel on both sides of joint 130. As finger 115 is bent, as illustrated in FIG. 2, an angle develops between the top of finger 115 on either side of joint 130. If a person fully bends his or her finger, an angle of approximately 90 degrees is formed between the top of the finger on either side of the joint.

Emitter 105, which can be a light source, can be placed on top of finger 115 on one side of joint 130 and can introduce or send light into finger 115 at a 45 degree angle towards joint 130. Light sources can include light generation sources and/or light generation devices, among others. Introducing light into a finger can include sending the light into the finger and/or causing the light to enter the finger. Sensor 110, which can be a light sensing device, can be placed on the top of finger 115 on the other side of joint 130 angled to receive light at a 45 degree angle towards joint 130. When finger 115 is straightened, as is illustrated in FIG. 1, the emitter emits and sends light generally towards the bottom of finger 115 under joint 130 such that much of the light will exit finger 115 on the bottom side of finger 115 approximately under joint 130. However, per the discussion above related to the reflectance method, some of the light from emitter 105 will be scattered and reflected towards sensor 110, and sensor 110 can receive this scattered and reflected light.

As finger 115 is bent at joint 130, as is illustrated in FIG. 2, increasing amounts of light emitted and sent by emitter 105 become generally directed towards sensor 110. In addition to any light received by reflectance, increasing amounts of the light emitted and sent by emitter 105 will pass directly through the tissue to sensor 110 via the transmission method due to the increasing bend of finger 115. This increases the amount of the light from emitter 105 that is received by sensor 110. This change in the amount or intensity of the light sent by emitter 105 that is detected by sensor 110 can be used as an indirect way to determine the angle of joint 130. One method of determining flexure of a joint is to determine the angle of a joint. As one having ordinary skill in the art will appreciate, determining flexure of a joint can be done using methods other than determining the angle of the joint. With emitter 105 and sensor 110 at 45 degree angles to the skin towards joint 130, as finger 115 is bent and joint 130 reaches 90 degrees, emitter 105 and sensor 110 will become parallel (i.e. emitter 105 will emit and send light at an angle parallel to the angle at which sensor 110 is angled to receive light). While this embodiment utilizes an angle of 45 degrees, a person having ordinary skill in the art will appreciate that the apparatus of FIG. 1 can work with many other angles.

Further, transmission of light through living tissue, such as a finger, is affected by the characteristics of the skin and tissue through which the light passes. As the finger flexes and the joints of the finger change angle, the characteristics of the tissue or the skin between two points on the skin can change, and the position of bones in the tissue can change, which can change the transmission of light between these two points. For example, the compression of the tissue can change, and, since the compression of tissue affects the transmission of light through the tissue, the light transmission between the two points can be affected. As another example, the tissue can deform as the finger flexes, changing the distance and amount of tissue between the two points, which also affects transmission of light between the two points. These changes in characteristics and the associated changes in light transmission can also be used as an indirect way of determining the angle of the joint.

Living tissue has optical properties which are defined by varying rates of absorption, attenuation, scattering, transmission, and reflection. Different imaging techniques, such as optical coherence tomography (OCT), laser Doppler flowmetry (LDF), and transmissive laser speckle imaging (TLSI) rely upon an understanding of these complex optical properties. The transmission of light into and through living tissue can depend on parameters such as the wavelength, intensity, and polarization of the light, the coherence of the light source, and the tissue compression, among others. The transmission can further depend on parameters and features of the tissues, such as pigmentation, fibrotic structure, hydration, composition, thickness, bone location and position, and the surges in blood flow associated with heartbeats. The transmission can additionally depend on external factors such as the location of the light emitter and sensor relative to the tissue, and the presence and characteristics of hair and clothing.

Figure 4:
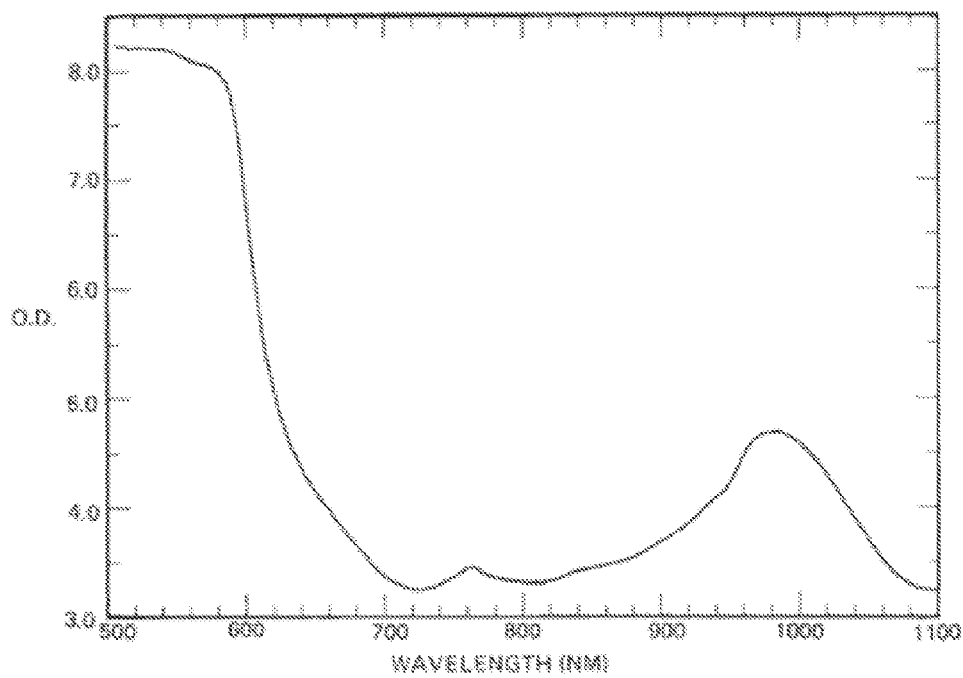
FIG. 4 is a graph of the Optical Density of a human hand versus the wavelength of the light.

The graph of FIG. 4 illustrates the Optical Density of a human hand versus the wavelength of the light. The Y-axis of this graph is the Optical Density, which reflects the transmission of light through a human hand. For example, an Optical Density of 3.5 corresponds to a percent transmission of light of about 0.5%. The X-axis of this graph is the wavelength of the light. As can be seen from the graph of FIG. 4, the best transmission through a hand is approximately between light wavelengths of 670 nm and 910 nm, and then from 1050 nm and up.

The light emitter and sensor can utilize various wavelengths of light, and even multiple wavelengths of light. An advantageous aspect of infrared wavelengths is that infrared wavelengths do not create distracting visible light in dark environments. In some embodiments, emitter 105 emits and sends light of one wavelength, and sensor 110 detects light of this same wavelength. As previously discussed, the characteristics of light sent into and through tissue, such as into and through finger 115, is affected by factors such as the tissue compression and the deformation of the tissue and change in bone position with finger flexing, among other factors. For example, the transmission or attenuation of light through finger 115 can be affected by the tissue compression of finger 115, or by the change in the amount of tissue between emitter 105 and sensor 110 that occurs when the tissue deforms as finger 115 is flexed. Because of these effects, one or more of the characteristics of the light that passes through finger 115, as determined using the readings of sensor 110, can be used to determine the angle of joint 130 of finger 115.

In some embodiments, emitter 105 sends light of multiple wavelengths, and sensor 110 detects light of these same multiple wavelengths. In some embodiments, multiple emitters and sensors are used, with each emitter and sensor pair sending and receiving the same wavelength of light, the wavelength being different from other emitter sensor pairs. In these multiple wavelength embodiments, in addition to using the one or more characteristics of the light as is discussed above, the ratio between these one or more characteristics of the light at these multiple wavelengths can be used to determine the angle of joint 130 of finger 115. For example, if emitter 105 emits both red and infrared light and sends the light into tissue, the ratio of one or more characteristics of this light upon exit from the tissue, such as the transmission or attenuation though the tissue, can be determined. Using data captured by sensor 110, the transmission and attenuation of both the red light and the infrared light exiting the tissue can be determined. The ratio of the two transmission values, or of the two attenuation values, can be determined and used to determine one or more characteristics of the tissue, such as the compression of the tissue of finger 115, which can be used to determine the angle of joint 130 of finger 115.

FIG. 2 illustrates an apparatus for determining an angle of a joint in a finger, shown with the finger bent. As illustrated in FIG. 2, the apparatus includes emitter 105, sensor 110, electronics module 120, connector 125, and glove 135. Electronics module 120 is coupled to emitter 105 and sensor 110 by connector 125. Electronics module 120 provides power to and communicates with emitter 105 and sensor 110 via connector 125. Electronics module 120 can cause emitter 105 to send light into finger 115. Upon entering finger 115, some light can be scattered and reflected, and a portion of the scattered and reflected light exits finger 115 and is received by the sensor 110, as per the above discussion of the reflection method. Some light can also passes through the tissue of finger 115 and be received by sensor 110, as per the above discussion of the transmission method. The amount of light sent by emitter 105 that is received by sensor 110 via the transmission method increases as finger 115 goes from being straight to being fully bent. Sensor 110 communicates the sensor readings to electronics module 120. Electronics module 120 includes a processor coupled to a memory, in some embodiments a non-volatile memory such as flash memory. The processor can use the readings from sensor 110, along with other information, to determine the angle of joint 130 of finger 115.

Figure 3:
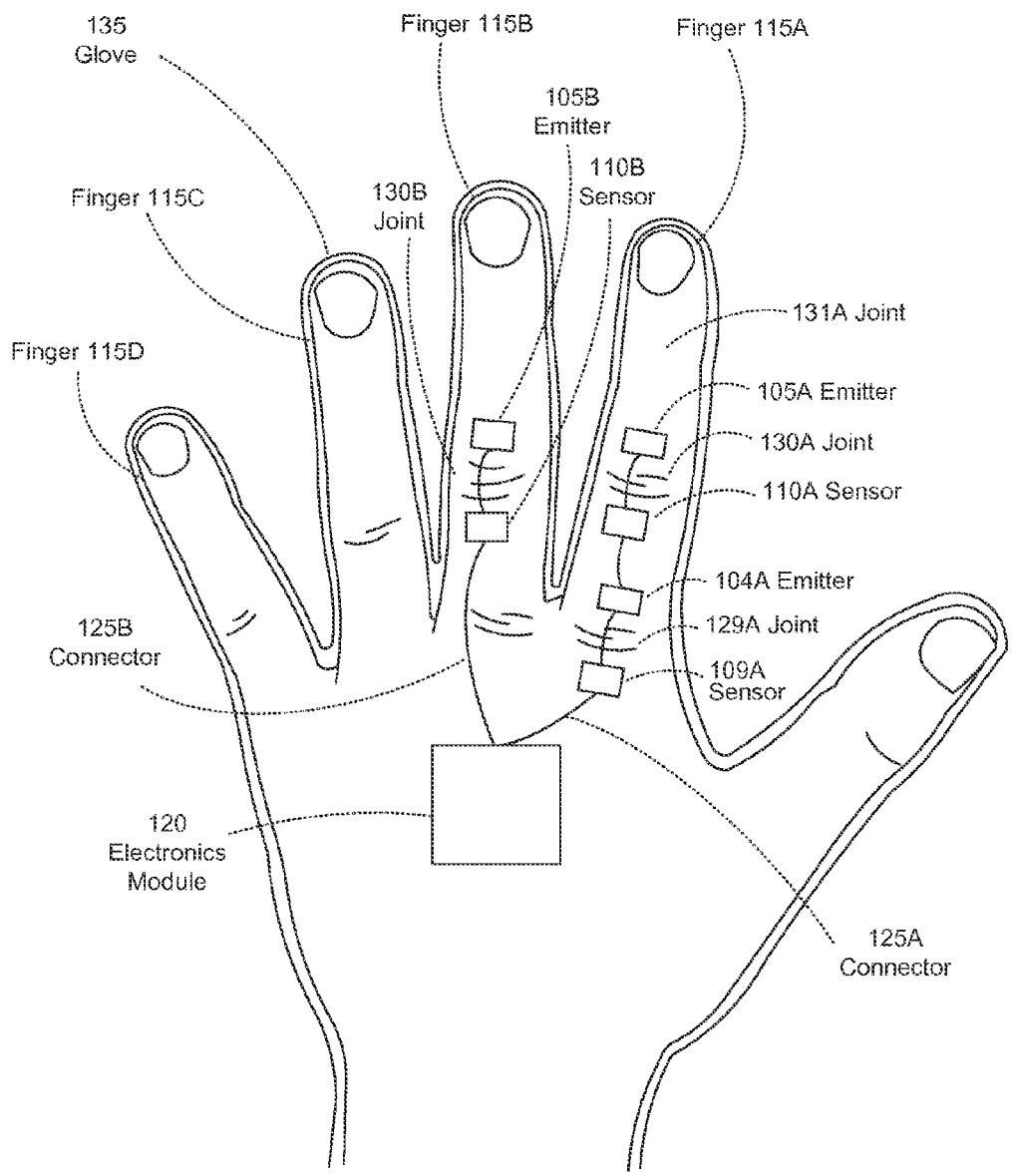
FIG. 3 illustrates an apparatus for determining an angle of multiple joints in multiple fingers.

FIG. 3 illustrates an apparatus for determining angles of multiple joints in multiple fingers. Depending on the intended application, angles of multiple joints on a finger or multiple fingers can be measured, with sensors and emitters on fingers as required. As illustrated in FIG. 3, emitter 105A and sensor 110A measure the angle of joint 130A (the second joint) on finger 115A, while emitter 104A and sensor 109A measure the angle of the joint 129A (the first joint). Generally it is not necessary to measure the third joint of a given finger, for example joint 131A, as the angle of the third joint tends to be linked to the angle of the second joint. The emitter/sensor pairs on finger 115A are coupled by connector 125A to electronics module 120, which can provide power to and communicate with the emitters and sensors.

As further depicted in FIG. 3, joint 130B of finger 115B is measured by emitter 105B and sensor 110B, and is coupled by connector 125B to electronics module 120, which can provide power to and communicate with the emitter and sensor. It is readily apparent to one of ordinary skill that additional sensor/emitter pairs can be placed to measure angles of joints in the thumb, finger 115C, and finger 115D, as the intended application requires, at the expense of additional complexity and cost.

Upon entering finger 115A/115B, some light can be scattered and reflected, and a portion of the scattered and reflected light can exit finger 115A/115B and be received by sensors 109A/110A and 110B respectively, as per the above discussion of the reflection method. Some light can also passes through the tissue of finger 115A/115B and can be received by sensors 109A/110A and 110B respectively, as per the above discussion of the transmission method. The amount of light sent by emitters 104A/105A and 105B that is received by sensors 109A/110A and 110B respectively via the transmission method increases as finger 115A/115B respectively goes from being straight to being fully bent. Sensors 109A/110A and 110B can communicate the sensor readings to electronics module 120. Electronics module 120 can include a processor coupled to memory. The processor can use the readings from sensors 109A/110A and 110B, along with other information, to determine the angles of joints 129A/130A and 130B of finger 115A/115B respectively.

Figure 5A:
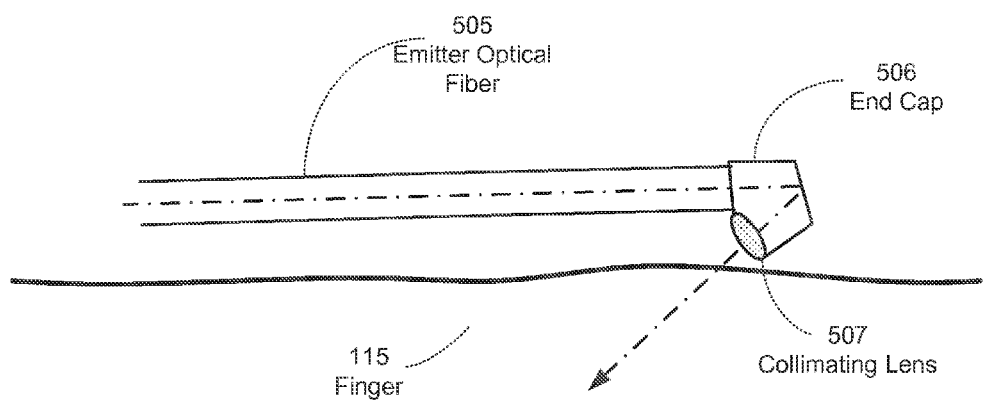
FIG. 5A illustrates an optical fiber used to send light from a light source into a finger.

FIG. 5A illustrates an optical fiber used to send light from a light source into a finger at a first angle. In FIG. 1, emitter 105 can be the light source, and the light source can be located at the point of entry or introduction of the light into finger 115. In the embodiment of FIG. 5A, the light source is not located at the point of entry, but is located remotely, for example in electronics module 120, and can be an infrared-spectrum light-emitting diode (LED). An advantageous aspect of this configuration is that all electrical elements may be contained within a sealed compartment, such as within electronics module 120. The light is sent from the light source via emitter optical fiber 505 to the point of entry of the light into finger 115.

In some embodiments, the end of emitter optical fiber 505 is fitted into end cap 506. End cap 506 contains collimating lens 507 and an angled reflective surface such that the light sent from the light source is reflected at a first angle (for example, 135 degrees) towards finger 115. The reflected light passes through collimating lens 507 before exiting end cap 506. In some embodiments, the end of emitter optical fiber 505 is turned and mechanically held at the first angle such that the light sent from the light source passes through a collimating lens and enters finger 115 at an appropriate angle.

Some applications require the measure of joint angles in harsh environments. For example, an application may measure joint angles with the hand immersed in water. With all electrical elements contained in a sealed compartment, the hand can be placed in a harsh environment, such as water, with higher robustness and reliability than an apparatus for measuring a joint angle where electrical components, such as electrical connectors, sensors, and emitters, may be immersed. Further, electronics module 120 can be located such that it is not immersed in water during typical usage, further increasing the robustness and reliability of measuring joint angles in harsh environments.

Figure 5B:
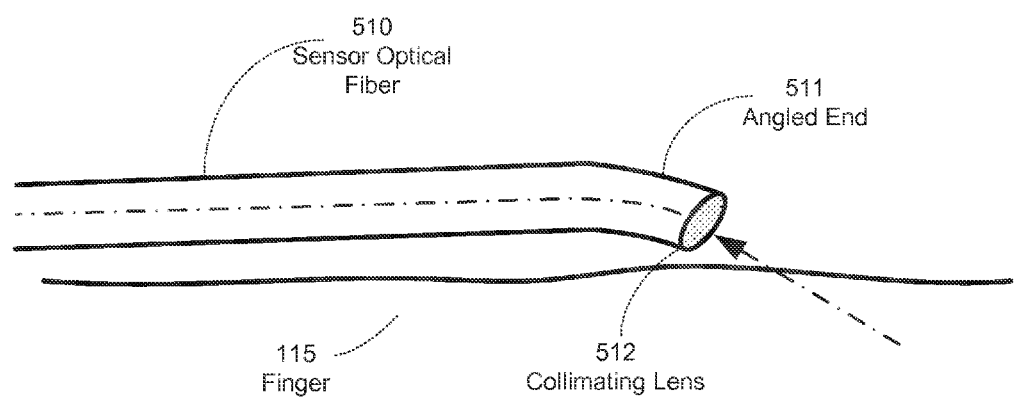
FIG. 5B illustrates an optical fiber used to send light exiting a finger to a sensor.

FIG. 5B illustrates an optical fiber used to receive and send light exiting a finger to a sensor. In some embodiments, the end of sensor optical fiber 510 is turned and mechanically held at a second angle (for example 45 degrees) such that reflected light exiting finger 115 at the second angle enters angled end 511 of sensor optical fiber 510 through collimating lens 512. The light received by sensor optical fiber 510 can then be sent by sensor optical fiber 510 to, for example, a sensor located in electronics module 120. In some embodiments, the end of sensor optical fiber 510 is fitted into an end cap containing a collimating lens and an angled surface such that the light exiting finger 115 is received and directed into sensor optical fiber 510. The light received by the sensor optical fiber 510 can then be sent by the fiber to, for example, a sensor located in electronics module 120.

Figure 6A:
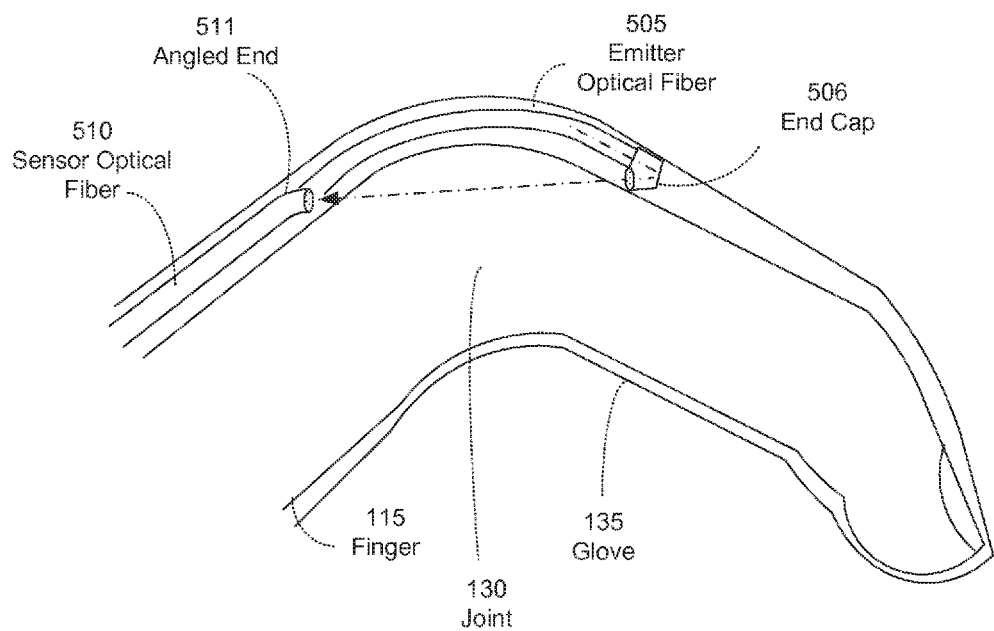
FIG. 6A illustrates optical fibers used to send light from a light source into a finger and to send light exiting the finger to a sensor with the finger bent.

FIG. 6A illustrates optical fibers used to send light from a light source into a finger and to send light exiting the finger to a sensor with the finger bent. As illustrated in FIG. 6A, the apparatus includes emitter optical fiber 505, sensor optical fiber 510, and glove 135. Glove 135 can provide mechanical support for emitter optical fiber 505 and sensor optical fiber 510, such that the fibers will remain with glove 135 when removed from a hand, and the fibers will be placed at appropriate locations on the hand when glove 135 is worn.

Figure 6B:
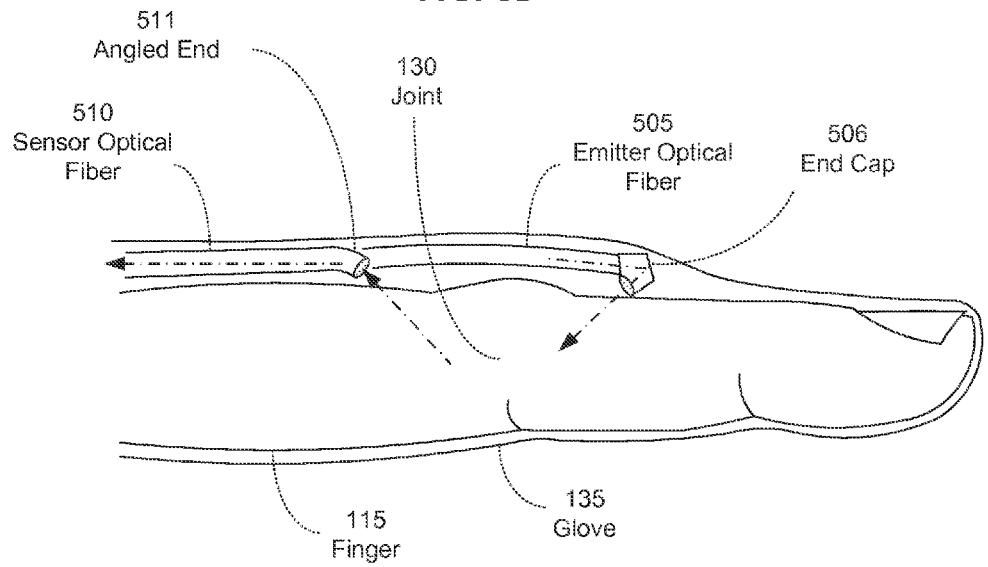
FIG. 6B illustrates optical fibers used to send light from a light source into a finger and to send light exiting the finger to a sensor with the finger straightened.

The apparatus of FIGS. 6A and 6B functions similarly to the apparatus of FIG. 1. For example, similar to FIG. 1, the movement of joint 130 changes the angle of the top of finger 115 on either side of joint 130. When finger 115 is straightened, as is illustrated in FIG. 6B, the top of finger 115 runs parallel on both sides of joint 130. As finger 115 is bent, as illustrated in FIG. 6A, an angle develops between the top of finger 115 on either side of joint 130. If a person fully bends his or her finger, an angle of approximately 90 degrees is formed between the top of the finger on either side of the joint.

Emitter optical fiber 505 can be placed on top of finger 115 on one side of joint 130. Light from a light source can be sent through emitter optical fiber 505 and turned at a 45 degree angle towards joint 130 by end cap 506. Sensor optical fiber 510 can be placed on the top of finger 115 on the other side of joint 130, with angled end 511 angled to receive light at a 45 degree angle from joint 130. When finger 115 is straightened, as is illustrated in FIG. 6B, the light exits emitter optical fiber 505 at an angle generally towards the bottom of joint 130 such that much of the light will exit the bottom of finger 115, reducing the light reaching sensor optical fiber 510. Sensor optical fiber 510 sends this received light to a sensor at the other end of the fiber, which may for example be housed in electronics module 120. While this embodiment utilizes an angle of 45 degrees, a person having ordinary skill in the art will appreciate that the apparatus of FIGS. 6A and 6B can work with many other angles.

As finger 115 is bent at joint 130, as is illustrated in FIG. 6A, increasing amounts of light exiting emitter optical fiber 505 become directed generally towards angled end 511 of sensor optical fiber 510. In addition to any light received by reflectance, as finger 115 is bent such that the angle of joint 130 approaches 90 degrees, increasing amounts of the light exiting emitter optical fiber 505 will be sent directly through the tissue of finger 115 to the end of sensor optical fiber 510. The increased intensity of the light thus detected by the sensor at the other end of sensor optical fiber 510 can be used as an indirect means to determine the angle of joint 130.

While optical fiber is used in the embodiment of FIGS. 6A and 6B, any clear medium capable of sending light can similarly be used. An optical fiber is a clear medium which can be flexible. An advantageous aspect of this technology is to provide an alternative to electromechanical methods that use wires and other components that can break with repeated flexing and pressure. Replacing the wires and other components of the electromechanical method with such a medium can enable higher reliability and improved robustness. For example, this replacement of the wires can enable locating all electronics in a sealed container where the electronics can be protected from the environment. Further, optical fibers do not have to be electromagnetically shielded.

Additionally, since the light can be sent over the clear medium, the sealed container containing the electronics can be located away from the joint. For example, the electronics container can be placed on the back of the hand or even further up the arm away from the finger joint. This can enable improved performance in harsh environments, as the electronics can be kept away and protected from the harsh environment. For example, an application may measure joint angles with the hand immersed in water. Being able to locate the electronics in a sealed container located away from the joint allows the electronics to be kept out of the water. The sealed container can further protect the electronics if any splashing of the water may happen, or can even protect the electronics sufficiently to enable full immersion in water.

Figure 7:
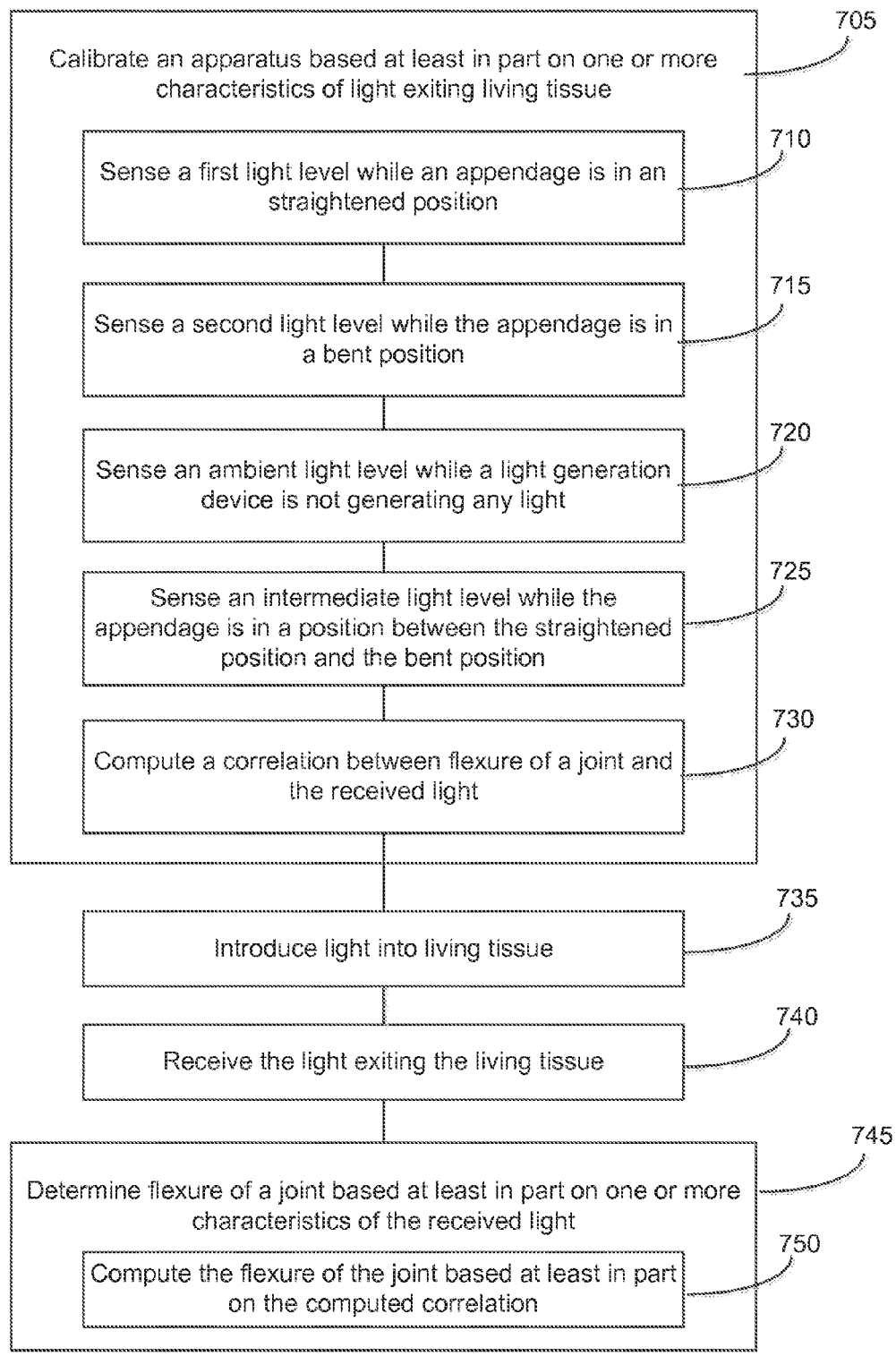
FIG. 7 is a flow chart illustrating exemplary operations for determining an angle of a joint in living tissue.

FIG. 7 is a flow chart illustrating exemplary operations for determining flexure of a joint in living tissue. In accordance with some embodiments of the present invention, the method illustrated in FIG. 7 can be performed using the embodiment illustrated in FIG. 1 as well as the embodiment illustrated in FIGS. 6A and 6B. The following description of FIG. 7 will be described with the method applied to the embodiments illustrated in FIG. 1 and FIG. 6A/6B. This is done with the intent of making the description of the method easier to follow.

Step 705 calibrates an apparatus based at least in part on one or more characteristics of light exiting living tissue. Steps 710, 715, 712, 725, and 730 are one set of steps that perform the calibration of step 705.

Step 710 senses a first light level while an appendage is in a straightened position. Referring to FIG. 1, emitter 105, controlled by electronics module 120, sends light into finger 115. Some of the light sent into finger 115 exits finger 115 and is received and sensed by sensor 110. Sensor 110 senses a first light level while finger 115 is in the straightened position.

Referring to FIGS. 6A and 6B as a second example, a light source controlled by an electronics module can send light into one end of emitter optical fiber 505, which can send the light into finger 115. Some of the light sent into finger 115 exits finger 115 and is received by sensor optical fiber 510, which sends the light to a sensor. The sensor can sense a first light level while finger 115 is in the straightened position.

Step 715 senses a second light level while the appendage is in a bent position. Referring to FIG. 1, emitter 105, controlled by electronics module 120, sends light into finger 115, and some of the light sent into finger 115 exits finger 115 and is received and sensed by sensor 110. Sensor 110 senses a second light level while finger 115 is in the bent position.

Using the embodiment of FIGS. 6A and 6B as a second example, a light generation source controlled by an electronics module can generate light and send the light into one end of emitter optical fiber 505, which can send the light into finger 115. Some of the light sent into finger 115 exits finger 115 and is received by sensor optical fiber 510 and sent to a sensor, which can sense a second light level while finger 115 is in the bent position.

Step 720 senses an ambient light level while a light generation device is not generating any light. Using the embodiment of FIG. 1 as an example, finger 115 can be the appendage. Emitter 105, controlled by electronics module 120, is turned off and is not sending any light into finger 115. Sensor 110 senses an ambient light level while emitter 105 is turned off.

Using the embodiment of FIGS. 6A and 6B as a second example, finger 115 can be the appendage. A light generation source controlled by an electronics module is turned off and is not sending any light into emitter optical fiber 505. Ambient light is received by sensor optical fiber 510 and can be sent to a sensor, which can sense an ambient light level while the light generation source is turned off.

Step 725 senses an intermediate light level while the appendage is in a position between the straightened position and the bent position. Using the embodiment of FIG. 1 as an example, finger 115 can be the appendage. FIG. 1 depicts finger 115 in a straightened position and FIG. 2 depicts finger 115 in a bent position. Finger 115 is in an intermediate position between the straightened position and the bent position. Emitter 105, controlled by electronics module 120, sends light into finger 115, and some of the light sent into finger 115 exits finger 115 and is received and sensed by sensor 110. Sensor 110 senses an intermediate light level while finger 115 is in the intermediate position.

Using the embodiment of FIGS. 6A and 6B as a second example, finger 115 can be the appendage. FIG. 6B depicts finger 115 in a straightened position and FIG. 6A depicts finger 115 in a bent position. Finger 115 is in an intermediate position between the straightened position and the bent position. A light generation source controlled by an electronics module can generate light and send the light into emitter optical fiber 505, which can send the light into finger 115. Some of the light sent into finger 115 exits finger 115 and is received and sent to a sensor by sensor optical fiber 510. The sensor can sense an intermediate light level while finger 115 is in the intermediate position.

Step 730 computes a correlation between flexure of a joint and the received light. Using the embodiment of FIG. 1 as an example, electronic module 120 can include a processor coupled to memory. The one or more characteristics of light exiting the living tissue can be a light level sensed by sensor 110, the sensed light sent by emitter 105. The processor can compute a function, such as a curve, to estimate flexure of joint 130 based on two or more of the light levels, also referred to as light intensities, sensed during steps 710, 715, 720, and 725. The processor, configured to perform step 730 via instructions stored in the memory, the instructions containing information regarding the flexure of joint 130 during steps 710, 715, 720, and 725, can use this flexure of joint 130 information and the light intensities sensed during steps 710, 715, 720, and 725 to compute a function approximating the flexure of joint 130 at other light intensities.

Step 735 introduces light into living tissue. Using the embodiment of FIG. 1 as an example, the living tissue can be finger 115. An emitter, such as emitter 105 controlled by electronics module 120, emits and sends light into finger 115, thereby introducing light into the living tissue of finger 115. Using the embodiment of FIGS. 6A and 6B as a second example, the living tissue can be finger 115. A light generation source controlled by an electronics module can generate and send light into one end of emitter optical fiber 505, which can send the light into finger 115, thereby introducing the light into the living tissue of finger 115.

Step 740 receives the light exiting the living tissue. Using the embodiment of FIG. 1 as an example, the living tissue can be finger 115. Emitter 105, controlled by electronics module 120, sends light into finger 115, and some of the light sent into finger 115 exits finger 115 and is received and sensed by sensor 110. Sensor 110 receives the light exiting the living tissue.

Using the embodiment of FIGS. 6A and 6B as a second example, the living tissue can be finger 115. A light generation source controlled by an electronics module can generate light and send the light into one end of emitter optical fiber 505, which can send the light into finger 115. Some of the light sent into finger 115 exits finger 115 and is received and sent by sensor optical fiber 510 to a sensor, where the light is received and sensed by the sensor.

Step 745 determines flexure of a joint based at least in part on one or more characteristics of the received light. One method of determining flexure of a joint is to determine the angle of a joint. As one having ordinary skill in the art will appreciate, determining flexure of a joint can be done using methods other than determining the angle of the joint. The one or more characteristics of the received light can include an intensity of the received light. Step 750 is one embodiment that performs the determination of step 745.

Step 750 computes the flexure of the joint based at least in part on the computed correlation. Using the embodiment of FIG. 1 as an example, electronics module 120 can include a processor coupled to memory. The computed correlation can be the computed correlation of step 730. Sensor 110 at step 740 receives and senses the intensity of the light. The processor can determine the flexure of joint 130 based on the sensed intensity of the light by computing the flexure of joint 130 based at least in part on the computed correlation of step 730.

Using the embodiment of FIGS. 6A and 6B as a second example, an electronics module can be coupled to optical emitter fiber 605 and sensor optical fiber 510. The electronics module can include a processor and a memory with the processor coupled to emitter optical fiber 505 and sensor optical fiber 510 (i.e. the processor is coupled to a light source and the light source is coupled to emitter optical fiber 505, therefore the processor is coupled to emitter optical fiber 505 via the light source). The computed correlation can be the computed correlation of step 730. Sensor optical fiber 510 receives the light exiting the living tissue and sends the light to a sensor, which senses the intensity of the light. The processor can determine the flexure of joint 130 based on the sensed intensity of the light by computing the flexure of joint 130 based at least in part on the computed correlation of step 730.

Although the present invention is described herein with reference to the preferred embodiment, one skilled in the art will readily appreciate that other applications may be substituted for those set forth herein without departing from the spirit and scope of the present invention. Accordingly, the present invention should only be limited by the Claims included below.

What is claimed is:

1. A method for determining flexure of a joint in living tissue comprising:
    with a light source, introducing light into said living tissue proximate to the joint;
    with a light sensing device, receiving said light exiting said living tissue proximate to the joint;
    with a processing device coupled to the light sensing device, receiving a signal that represents a characteristic of said received light;
    with the processing device, analyzing the signal that represents the characteristic of said received light to detect a change in optical density resulting from said flexure of said joint; and
    with the processing device, determining a flexure of said joint based at least in part on the change in the optical density.

2. The method of claim 1, wherein said light introduced into said living tissue is sent from said light source to a point of introduction of said light into said living tissue by a first optical fiber, and wherein said light received by said light sensing device is sent from a point of exit of said light from said living tissue to said light receiving device by a second optical fiber.

3. The method of claim 1, further comprising:
    calibrating an apparatus based at least in part a characteristic of said received light exiting said living tissue.

4. The method of claim 1, wherein the characteristic of said received light is intensity of said received light, and wherein the change in the optical density is detected based at least in part on a change in the intensity of said received light between the introduced light and the received light.

5. The method of claim 3, wherein said joint is part of an appendage, wherein said calibrating said apparatus further comprises:

sensing a first light level while said appendage is in a straightened position;

sensing a second light level while said appendage is in a bent position; and computing a correlation between said flexure of said joint and said received light, said computed correlation based at least in part on said sensed first light level and said sensed second light level.

6. The method of claim 5, wherein said calibrating said apparatus further comprises:

sensing an ambient light level while said light source is not generating any light; and sensing an intermediate light level while said appendage is in a position between said straightened position and said bent position, wherein said computing said correlation is further based at least in part on said sensed ambient light level and said sensed intermediate light level.

7. The method of claim 5, wherein said determining said flexure of said joint further comprises:

computing said flexure of said joint based at least in part on said computed correlation.

8. The apparatus of claim 1, wherein said determining said flexure of said joint further includes determining an angle of said joint.

9. An electronic storage medium having stored therein program instructions which, when executed by a processing device, implement the method of claim 1.

* * * * *